United States Patent [19]

Fukuda et al.

[11] Patent Number: 4,702,910
[45] Date of Patent: Oct. 27, 1987

[54] COMMON ANTIGEN (PSC-A) TO PSEUDOMONAS AERUGINOSA WHICH ACTS AS AN AGENT FOR PRETECTING PSEUDOMONAS AERUGINOSA INFECTION

[75] Inventors: Tamotsu Fukuda, Chiba; Shiro Shigeta, Fukushima; Hiroaki Okuya, Chiba; Yasuyuki Kuroiwa, Chiba; Tadashi Sudo, Chiba, all of Japan

[73] Assignee: Mitsui Toatsu Chemicals, Inc., Tokyo, Japan

[21] Appl. No.: 797,796

[22] Filed: Nov. 14, 1985

[51] Int. Cl.$^4$ .................... A61K 39/104; C07K 15/04
[52] U.S. Cl. .......................... 424/92; 424/88; 530/350; 530/352; 530/395; 530/825; 435/68
[58] Field of Search ................ 424/88, 92; 530/350, 530/352, 395, 825; 435/68

[56] References Cited

U.S. PATENT DOCUMENTS

| | | | |
|---|---|---|---|
| 4,428,931 | 1/1984 | Tolman et al. | 424/85 |
| 4,575,459 | 3/1986 | Homma et al. | 424/85 |
| 4,578,458 | 3/1986 | Pier | 424/88 |

FOREIGN PATENT DOCUMENTS 2290219  6/1976  France .

*Primary Examiner*—John Kight
*Assistant Examiner*—Garnette D. Draper
*Attorney, Agent, or Firm*—Browdy and Neimark

[57] ABSTRACT

PSC-A is a new serological common antigen to *Pseudomonas aeruginosa* having very low toxicity, and highly effective for protecting infection by any of the serotypes of *Pseudomonas aeruginosa*. PSC-A can be used as the active component in a pharmaceutical agent for protecting *Pseudonomas aeruginosa* infection.

3 Claims, 1 Drawing Figure

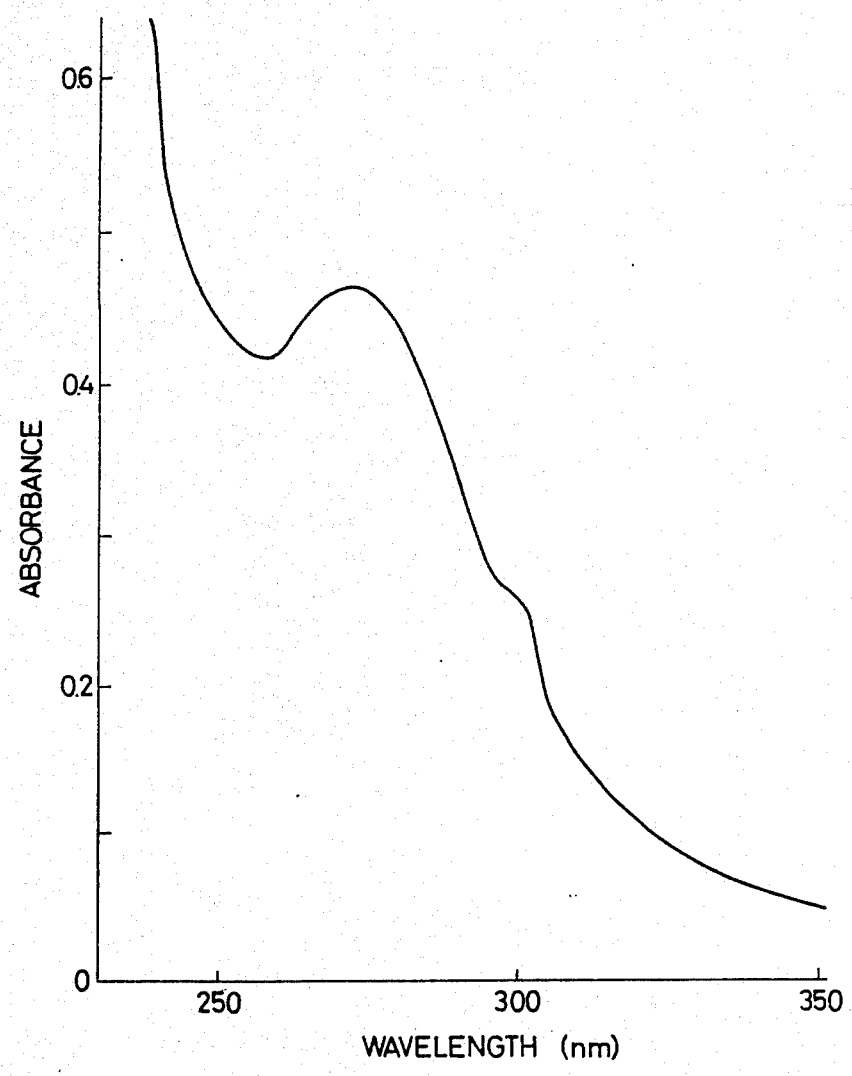

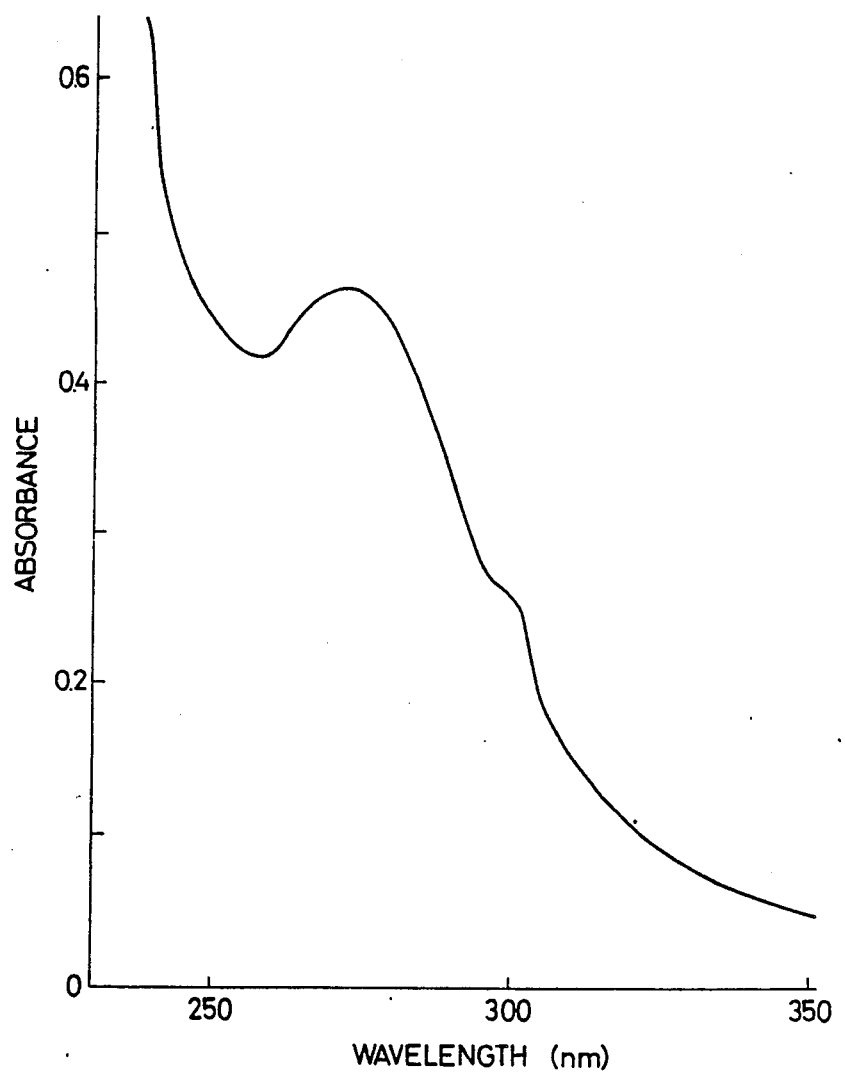

COMMON ANTIGEN (PSC-A) TO *PSEUDOMONAS AERUGINOSA* WHICH ACTS AS AN AGENT FOR PRETECTING *PSEUDOMONAS AERUGINOSA* INFECTION

FIELD OF THE INVENTION

This invention relates to PSC-A, a new common antigen to *Pseudomonas aeruginosa* (hereafter abbreviated as *P. aeruginosa*) and is effective for protecting *P. aeruginosa* infection.

BACKGROUND OF THE INVENTION

*P. aeruginosa* is originally known as an attenuated pathogenic bacterium. In accordance with the recent increase in the rate of occurrence of bacterial replacement and proliferation resulting from the administration of large doses of antibiotics, the number of patients infected by *P. aeruginosa* as distinct from other bacterical infectious diseases has notably increased.

*P. aeruginosa* easily causes infectious disease in patients having reduced resistance to infection, and therefore this infectious disease is one of the representative opportunistic infectious diseases. The above patients having reduced resistance to infection include patients with cancer, those receiving immunosuppressive therapy, implantation patients, burn patients, and infants.

After once occuring, the acute disease caused by this bacterum has a strong tendency to develop into a systemic infection. Also a good prognosis for this disease can not be expected. Therefore this disease has come to be numbered as one of the most difficient to cure cured bacterial infectious diseases.

Infectious diseases caused by *P. aeruginosa* are generally difficult to cure for the following reasons:

(1) This bacterium exhibits a high resistance to almost all of the antibiotics which have been typically used.

(2) This bacterium tends to be resistant to recently developed antibiotics which are effective against *P. aeruginosa*.

(3) There is a high incidence of infectious diseases caused by *P. aeruginosa* which can not be satisfactorily treated by chemotherapy using these antibiotics.

On the basis of the fact that there is a limit to the chemotherapy of infectious diseases caused by *P. aeruginosa* performed using antibiotics, several attempts have been made to develop vaccines or infection-protective agents which are prepared from cell components of *P. aeruginosa* and used to increase the ability of the host to protect itself against *P. aeruginosa*.

For instance, the polyvalent vaccine PEV-01 protective against all serotypes of *P. aeruginosa* was prepared by purifying the superficial antigen of each serotype of *P. aeruginosa* (specific antigen for each serotype) and mixing the purified superficial antigens (Lancet II; 977, 1979). After performing an attempt to clinically apply this polyvalent vaccine to burn patients, it was reported that this vaccine is protective against septicemia by *P. aeruginosa* infection.

However, the preparation of this polyvalent vaccine is complicated by mixing more than 10 antigens against different serotypes of *P. aeruginosa*. Besides, since the specific antigens of different serotypes which are components of this vaccine are so-called O antigens existing in the surface layers of cells of *P. aeruginosa* and are composed of lipopolysaccharides called endotoxin, this vaccine cause unavoidably local and systemic side effects such as intense pyrogenecity.

OEP (original endotoxin protein) principally composes of protein was isolated as a serological common antigen to *P. aeruginosa* by Homma et al. It was reported that OEP works as an protective antigen common to all serotypes of *P. aeruginosa* and can be used for vaccine (Jpn. J. Exp. Med.; 47, 393–402, 1977).

Homma et al. thought that this infection can not satisfactorily be protected by OEP alone and carried out each clinical experiment by a vaccine consisting of a mixture of toxoids prepared by combining OEP with two or three components among protease, elastase and exo toxoid from *P. aeruginosa*. Although it was reported that these vaccines showed good effect in some cases, they have not yet been put to practical use.

The other vaccines of *P. aeruginosa* include ribosome vaccines each having a specific effect against each serotype of the bacterium, pili vaccines characterized by adhering to the surface of membrane, and flagella vaccines which stop the movement of bacteria. However, all of these vaccines are still in the experimental stage. Therefore, it is no exaggeration to say that the appearance of excellent vaccines against *P. aeruginosa* infection is still desired.

SUMMARY OF THE INVENTION

During investigations which have been performed to find a new infection-inhibiting antigen which by itself has the ability to protect against *P. aeruginosa* infection and acts upon all serotypes of *P. aeruginosa*, the inventors succeeded in preparing a mouse-hybridoma which produces a monoclonal antibody which can react with serotypes of *P. aeruginosa*. Additionally, the authors first discovered that the cell component of *P. aeruginosa* corresponding to the above monoclonal antibody has great ability to protect infection by all serotype of *P. aeruginosa*.

Specially, during a study performed to prepare a hybridoma which can produce an anti-*P. aeruginosa* monoclonal antibody through the cell fusion between spleen cells of mice immunized with *P. aeruginosa* and mouse myeloma cells, the inventors succeeded in producing a hybrid cell line which can produce a monoclonal antibody to react with all serotypes of *P. aeruginosa* (hereafter referred to as C-Ab-producing hybridoma). After that, the inventors isolated and purified the cell component of *P. aeruginosa* corresponding to the monoclonal antibody produced by the C-Ab-producing hybridoma (hereafter referred to as C-Ab) by an affinity chromatography using immobilizing C-Ab. The common antigen obtained thus to *P. aeruginosa* which can react with C-Ab was found to be a completely new substance composed of protein, has ver low toxicity, and exhibits excellent ability in an animal experiment to protect infection by all serotypes of *P. aeruginosa*, resulting in this invention.

The substance of this invention will be simply referred to as PSC-A hereafter.

This invention relates to PSC-A, a new common antigen to *P. aeruginosa* which is protective against *P. aeruginosa* infection. More specifically, this invention relates to the new common antigen, PSC-A, which is obtained from *P. aeruginosa*, and has the ability to protect *P. aeruginosa* infection as well as the preparation of PSC-A and an agent for protection against *P. aeruginosa* infection.

This invention also relates to a method for preparing the common antigen PSC-A to *P. aeruginosa* having the ability to protect *P. aeruginosa* infection from a cell-free extract, which is obtained by crushing *P. aeruginosa* before centrifuging, through isolation and purification using an affinity chromatography by immobilizing the monoclonal antibody with a specific affinity for the common antigen PSC-A.

This invention also relates to an agent for protecting *P. aeruginosa* infection which contains the common antigen PSC-A as its active component.

The purpose of this invention is to supply an agent for protecting *P. aeruginosa* infection, which contains the common antigen PSC-A from *P. aeruginosa* as its active component for the vaccinotherapy of animals and humans.

BRIEF DESCRIPTION OF THE DRAWING

The FIGURE shows an ultraviolet spectrum for PSC-A.

DETAILED DESCRIPTION OF THE INVENTION

This invention will be concretely described in the following.

All strains of *P. aeruginosa* used in this invention are listed according to serological classification in Table 1. There are different theories about the classification of *P. aeruginosa*. The strains of *P. aeruginosa* used in this invention, are classified according to serological classification given in the report of the serotyping committee of the Japan *P. aeruginosa* society (1975, Japan J, Exp. Med., 46, 329, 1976). All strains belonging to A~M groups according to this classification can be used as a specific serotype of *P. aeruginosa* described in this invention. Since it was thought to be the best method, the classification of *P. aeruginosa* for this invention was performed according to the serological classifications established by the serotyping committee. Considering that new classification criteria will be adopted in the future, it can be said that the strains of *P. aeruginosa* which can be used in this invention, include all bacterial strains having PSC-A as an infection-protecting antigen.

Thus, the bacterial strains which can be used in this invention are not restricted to those belonging to the above groups A~M or those which can be classified according to this classification criteria. Here, among the strains of *P. aeruginosa* belonging to groups A~M and listed in table 1, most of the IID strains are registered in the American Type culture Collection (catalogue of BACTERIA-PHAGES-γDNA VECTORS 16th edition, page 136, 1985), that is an American organization for preserving bacterial strains, and can be supplied from this organization.

TABLE 1

| Classification established by Japan *P. aeruginosa* society | Strain |
| --- | --- |
| A *P. aeruginosa* | IID 1001 (ATCC 27577) |
| B *P. aeruginosa* | IID 1002, ATCC 27578, IID 1007 ATCC 27583, IID 1013, ATCC 27589, IID 5004 |
| C *P. aeruginosa* | IID 1003, ATCC 27579, IID 1037, IID 1021 |
| D *P. aeruginosa* | IID 1004 (ATCC 27580) |
| E *P. aeruginosa* | ATCC 27581, IID 1130, PA 103 |
| F *P. aeruginosa* | IID 1006 (ATCC 27582) |
| G *P. aeruginosa* | ATCC 10145, ATCC 27584, P 28 |

TABLE 1-continued

| Classification established by Japan *P. aeruginosa* society | Strain |
| --- | --- |
| H *P. aeruginosa* | IID 1009 (ATCC 27585) |
| I *P. aeruginosa* | ATCC 27586 |
| J *P. aeruginosa* | IID 1011 (ATCC 27587) |
| K *P. aeruginosa* | IID 1012 (ATCC 27588) |
| L *P. aeruginosa* | IID 1014 (ATCC 27590) |
| N *P. aeruginosa* | IID 5018 |

The preparation and the property of the monoclonal antibody C-Ab having a specific affinity for PSC-A and used in an affinity chromatography used to isolate and purify PSC-A, will be described in Experimental Example 1.

EXPERIMENTAL EXAMPLE 1

PRODUCTION, PREPARATION AND PROPERTY OF MONOCLONAL ANTIBODY C-Ab

C-Ab-producing hybridoma was produced according to the well-known method by Kohler, Milstein et al. (Nature, 256, 495, 1975). After an emulsion of *P. aeruginosa* ATCC 27581 (E type) treated with 0.3% of formalin was prepared with Freund incomplete adjuvant, this emulsion was intraperitoneally administered to female BALB/C mouse (7 weeks old) every other week for a total of 5 times to achieve immunization. The $5 \times 10^3$ mouse spleen cells collected 4 days following the final immunization and $5 \times 10^7$ NS-1 mouse myeloma cells were subjected to cell fusion in the presence of 50% polyethylene glycol to produce a hybridoma. The hybridoma thus prepared was then poured into a 96-well flat bottom microplate and cultured on Dulbecco MEM medium supplemented with 10% fetal bovine serum containing HAT (hypoxanthine, amimopterin and thymidine) at 37° C. in the presence of 5% of $CO_2$. For wells in which proliferation of the hybridoma was observed, the presence of anit-*P. aeruginosa* monoclonal antibody in the culture solution was determined by Dot Immunobinding Assay which is an enzyme immunoassay (Anal. Biochem. 119, 142–147, 1982, hereafter referred to as DIBA method). DIBA method was performed using a 96-well microtiter plate according to the following procedure. A nitrocellulose membrane filter (3.1 mm square) prepared by immobilizing 0.4 μg per dot of *P. aeruginosa* treated with 0.3% of formalin (used as the antigen) was incubated with 100 μl of the above culture solution at room temperature for 30 minutes before being incubated with peroxidase-labelled anti-rabbit mouse immunoglobulin antibody (manufactured by DAKO company) for 30 minutes. The nitrocellulose membrane filter was then reacted with 4-chloro-1-naphtol as a substrate for peroxidase. A positive result was recorded when dark blue spot was observed on the membrane filter by immobilizing the antigen. When the production of the monoclonal antibody was detected in the culture solution, the hybridoma was further subjected to cloning by limiting dilution. The monoclonal hybridoma obtained thus was proliferation in a flask, and the proliferated monoclonal hybridoma was implanted in the abdominal cavity of a DALB/C mouse treated with the immunosuppressant Pristane (Aldrichi company). Thus ascites fluid of the treated mouse was applied to an affinity chromatography with Protein A-Sepharose (Pharmacia company) to prepare a purified monoclonal antibody. Among the hybridomas obtained thus which can produce various anti-*P. aeruginosa* monoclonal antibodies, the inventors found a C-Ab-producing hybridoma which can produce a monoclonal antibody C-Ab reacting with all the serotypes of *P. aeruginosa*. The reactivities of this C-Ab for several serotypes of *P. aeruginosa* determined by DIBA method are shown in Table 2. This C-Ab exhibited almost equal affinities for all serotypes of *P. aeruginosa*. Additionally, this C-Ab did not react with either the endotoxin from serotype E of *P. aeruginosa* [lipopolysaccharied, prepared from the ATCC 27581 strain (N-10 strain) of *P. aeruginosa* by the Morrison method (J. Biol. Chem., 250, 2911, 1977)], or OEP [prepared from the ATCC 27581 strain (N-10 strain) of *P. aeruginosa* by the method of Homma et al. (Japan J. Exp. Med., 42, 23, 1972)]. This result indicates that PSC-A has a property different from those of these substances.

The monoclonal antibody C-Ab shown in the above Experimental Example 1, as will be described later in detail, is essential for purification to achieve simple high-yield of PSC-A from *P. aeruginosa*. It is usual that C-Ab can be preferablly used after being immobilized with a carrier such as Affigel-10 (Bio-Rad company) or BrCN-Sepharose (Pharmacia company).

The antibody for the preparation of PSC-A is not restricted only to C-Ab shown in Experimental Example 1, and any antibodies having a specific affinity for PSC-A can be favorably used for the method of this invention. For example, monoclonal antibodies can be used for affinity chromatography, each having a specific affinity for PSC-A and produced by either a hybridoma through the cell fusion between myeloma cells and anti-PSC-A-antibody-producing B lymphoid cells from an animal newly immunized with PSC-A isolated in Examples 1~3 or an animal or human stimulated with PSC-A in vitro, or proliferation-type cells by infecting human B lymphoid cells to produce anti-PSC-A antibody with EB virus. Besides, mixtures of these antibodies as well as anti-PSC-A polyclonal antibody obtained from the serum of an animal immunized with PSC-A can also be used as antibodies for this invention.

TABLE 2

| Strain | Serotype | Titer of C-Ab determined by DIBA method |
| --- | --- | --- |
| *P. aeruginosa* IID1001 | A | $5^5 \times 10^2$ |
| *P. aeruginosa* IID1002 | B | $5^4 \times 10^2$ |
| *P. aeruginosa* IID1007 | B | $5^4 \times 10^2$ |
| *P. aeruginosa* IID1013 | B | $5^4 \times 10^2$ |
| *P. aeruginosa* IID5004 | B | $5^4 \times 10^2$ |
| *P. aeruginosa* IID1037 | C | $5^4 \times 10^2$ |
| *P. aeruginosa* IID1004 | D | $5^4 \times 10^2$ |
| *P. aeruginosa* IID1130 | E | $5^4 \times 10^2$ |
| *P. aeruginosa* ATCC27581 | E | $5^4 \times 10^2$ |
| *P. aeruginosa* PA103 | E | $5^4 \times 10^2$ |
| *P. aeruginosa* IID1006 | F | $5^4 \times 10^2$ |
| *P. aeruginosa* ATCC27584 | G | $5^4 \times 10^2$ |
| *P. aeruginosa* ATCC10145 | G | $5^4 \times 10^2$ |
| *P. aeruginosa* P-28 | G | $5^4 \times 10^2$ |
| *P. aeruginosa* IID1009 | H | $5^4 \times 10^2$ |
| *P. aeruginosa* ATCC27586 | I | $5^4 \times 10^2$ |
| *P. aeruginosa* IID1011 | J | $5^4 \times 10^2$ |
| *P. aeruginosa* IID1012 | K | $5^4 \times 10^2$ |
| *P. aeruginosa* IID1014 | L | $5^4 \times 10^2$ |

TABLE 2-continued

| Strain | Serotype | Titer of C-Ab determined by DIBA method |
| --- | --- | --- |
| *P. aeruginosa* IID5018 | M | $5^4 \times 10^2$ |

*1 Microbial cell from each serotype of *P. aeruginosa* treated with 0.3% of formalin was dotted on a nitrocellulose membrane filter.
*2 Classification of Japan *P. aeruginosa* Society.
*3 C-Ab-producing hybridoma was implanted in the abdominal cavity of a BALB/C mouse (8 week old) to obtain ascites fluid, and then the ascites fluid was subjected to centrifugation (30000 × g, 20 min, 4° C.) and supernatant was used for theactivity.
The antibody titer of C-Ab for each strain was expressed as the maximum multiple of dilution on C-Ab (supernatant of ascites) for which dark blue spot was observed on a nitrocellulose membrane filter.

Next, a basic method for producing PSC-A will be described. Strains of *P. aeruginosa* which can be used in producing PSC-A are as described above. Conventional methods for culturing *P. aeruginosa* and crushing microbial cells may be used. For the medium, heart infusion broth, brain heart infusion broth (manufactured by Eiken Kagaku), nutrient broth, or a synthetic medium prepared according to the method of Homma et al. (J. Biochem. 83, 711–18, 1978) can be used. The synthetic medium by Homma et al. without any proteins is specially preferable because there is no possibility for contamination of proteins in the medium into microbial component. It is preferable that the temperature of the medium remain between 25° C. and 37° C., and that its pH be between 6.5 and 8.5. The culture should be performed under aerobic conditions. For example, it is recommended that shaking culture or aerational agitation culture in a culture vessel should be performed. The culture period influences the yield of PSC-A from *P. aeruginosa*.

Usually a culture period of 16~24 hours is preferable. For example, after shaking culture at 37° C. for 24 hours on the synthetic medium (pH7.4) of Homma et al. microbial cells desired were obtained by centrifugation of filtration. Here, it is possible to recover these microbial cells after they are deactivated by being treated with a small amount of formalin. The microbial cells obtained thus are then sufficiently mixed with water or a proper buffer solution before being crushed by a DYNOMILL, a French press, an ultrasonicator while being coolled below 10° C. The suspension obtained thus is then decanted and subjected to centrifugation to obtain a cell-free extract of PSC-A. The centrifugation of the suspension is performed at 39,000×g for 30 minutes, and the supernatant is collected. In preparing a suspension by crushing microbial cells of *P. aeruginosa* by a machine, the rate for the extraction of PSC-A can be further improved by adding either a small quantity of a surfactant such as Triton X-100 a chelating agent such as EDTA or an enzyme such as lysozyme, deoxyribonuclease or ribonuclease.

The cell-free extract used in this invention refers to a fraction which is prepared by removing noncrushed microbial cells, partially crushed microbial cells, and the insoluble fraction of cell wall fraction from the suspension by centrifugation as much as possible. Crude PSC-A can be obtained from the cell-free extract by subjecting it to an ion-exchange column chromatography or a gel filtration chromatography. PSC-A can be easily obtained with a high yield according to the method used in this invention by isolating and purifying PSC-A by applying the cell-free extract to an affinity column prepared by immobilizing a monoclonal antibody such as C-Ab. It is preferable that a monoclonal antibody such as C-Ab with a specific affinity for PSC-A is used for the isolation and purification of PSC-A is used after immobilized with a proper carrier such as Affigel or CNBr-Sepharose as previously mentioned. The affinity column to which the cell-free extract was applied is then thoroughly washed with a neutral buffer with a pH of 6~8 to elute contaminants other than PSC-A which are not bound to the above immobilized monoclonal antibody. Next, a buffer of low pH range usually used for the dissociation of the antigen-antibody complex such as 50 mM glycine-HCl buffered physiological saline (pH 3.0) is used for the affinity column to dissociate and elute PSC-A bound to the monoclonal antibody. The eluate prepared thus is then adjusted pH to be neutral before the neutralized solution is dialyzed against distilled water. After that, the dialysate is lyophilized to obtain a pure powder of PSC-A.

The concentration of PSC-A in the filtrate from the culture can be neglected as long as microbial cells are obtained as a usual culture product of living bacteria. However, when a large amount of PSC-A has been transferred from microbial cells to a filtrate due to death or autolysis of microbial cells by a long period culture, it is possible to recover the purified PSC-A by applying a supernatant by centrifugation of the above filtrate to an affinity column prepared by immobilizing the above monoclonal antibody with a specific affinity for PSC-A.

In order to effectively elute and remove contaminants other than PSC-A from the affinity column to which the previous mentioned cell-free extract has been applied, washing the column with a neutral buffer with a small quantity of a surfactant such as Triton X100 is recommended.

The biophysical chemical properties of PSC-A obtained through purification in Example 1 will be shown in the following.

PSC-A obtained in Example 2 or Example 3 also exhibited the same properties.

Biophysical Chemical Properties of PSC-A Which is a Common Antigen to *P. aeruginosa*

(1) Molecular Weight

About 15,000 (by SDS-polyacrylamide gel electrophoresis) A single band stained by coomassie brilliant blue R250 was observed in polyacrylamide electrophoresis (PAGE) performed under each of the following conditions.

| Conditions for PAGE | | Result |
|---|---|---|
| pH 9.5 | 7% gel | Rf = 0.86 |
| pH 9.5 | 10% gel | Rf = 0.80 |
| pH 9.5 | 12% gel | Rf = 0.78 |

(2) Protein, Sugar and Hexosamine Content

Protein Content (%) : 55.0 [(colorimetric analysis by hydrolysis using ninhydrin, bovine serum albumin as the standard)(Anal. Biochem., 49, 95, 1972)] 27.0 [modified Lowry method, bovine serum albumin as the standard) (Anal. Biochem., 69, 646, 1975)], 24.0 [(protein binding assay, bovine serum albumin as the standard)(Anal. Biochem., 72, 248, 1976)].

Sugar Content (%) : 3.0~5.0 [(phenol-sulfuric acid method, glucose as the standard (Anal. Chem., 28, 350, 1956)].

Hexosamine Content (%) : below 1.0 [(Rondle. Morgan method, glucosamine as the standard)(Biochem. J., 61, 586, 1955)].

(3) Lipid Content (%) : 7.0~10.0 [(modified Bligh. Dyer method (Can. J. Biochem. physiol., 37, 911, 1959)].

The original spot is colored when the chloroform methanol extract of PSC-A (modified Bligh. Dyer method) is developed on a silica gel TLC by using a mixture of petroleum ether, ether and ocetic acid (80:20:1) before being colored by treating with 50 % sulfuric acid solution and heating it.

(4) Description and Solubility

The agent is a pale yellow powder soluble in water, physiological saline and phosphate buffer, and is water soluble with a solubility of 1 mg/ml or higher. It is almost insoluble in methanol, ethanol, hexane and chloroform.

(5) Coloring Reaction

Lowry, Folin reaction, ninhydrin reaction, phenol-sulfate reaction and anthron-sulfate reaction produce a positive result while Elson.Morgan reaction yields a negative result.

(6) Isoelectric Point pH 3.8~4.2 (agarose electrofocusing)

(7) Stability

Stable in a neutral aqueous solution at room temperature for at least 24 hours.

(8) Ultraviolet Spectrum

Maximum absorption occurs at about 272 nm as shown in FIG. 1.

(9) Enzymatic Activity

It does not cause the decompose of casein or collagen.

(10) Properties (i) When 10 μg/ml of PSC-A is added to L cells of a cell-line derived from mouse connective tissue before they are cultured for 24 hours of 2 μg/ml of PSC-A is added to leukocytc cells derived from the spleen of a normal mouse before they are cultured for 24 hours, PSC-A does not exhibit any direct toxicity for either the L cells or the Leukocyte cells.

(ii) For both a solution prepared by dissolving PSC-A in physiological saline and a emulsion prepared by mixing PSC-A with Freund incomplete adjuvant or Freund complete adjuvant, and antibody which can react with *P. aeruginosa* appears in the serum of a mouse immunized with PSC-A. Additionally, PSC-A treated with the proteolytic cnzyme pronase or heated at 100° C. for 10 minutes does not react with a serum from a mouse immunized with nontreated PSC-A.

(iii) The mouse monoclonal antibody having a specific affinity for PSC-A does not react with either the well-known common antigen OEP to *P. aeruginosa* or the endotoxin of *P. aeruginosa* (lipopolysaccharide).

When used as an agent for protecting against *P. aeruginosa* infection, it is preferable that this agent be administered by injection. A solution or a lyophilized preparation prepared from PSC-A alone or combining it with usual additive and excipient can be practically used. It is possible to incorporate PSC-A in an oil-in-water type emulsion or a water in-oil type emulsion. Also, PSC-A can be practically used either by sealing PSC-A in liposome composed of phospholipid, cholesterol or by fixing PSC-A to the outer surface of the membrane of liposome.

The dose and the administration route for PSC-A may be properly selected. It is preferable that the dose be 0.001~10 mg per kg body weight. For the administration route, intracutaneous, subcutaneous, intravenous, intramuscular and intraperitoneal administrations can be performed.

PSC-A has antigenicity which occurs in a so-called vaccine and induces the production of high concentration of an antibody for P. aeruginosa in the serum of a mouse or guinea pig immunized with PSC-A.

Furthermore, PSC-A is highly active for protecting animal P. aeruginosa infection. For example, mice immunized with PSC-A were not infected with a lethal does of each of all serotypes of P. aeruginosa and could live after being treated with P. aeruginosa. This indicates remarkable ability of PSC-A protect P. aeruginosa infection.

PSC-A has low acute toxicity because the 50% lethal does of PSC-A when it is intravenously administered to mice is more than 5 mg/kg. As shown in claim, PSC-A does not cause any direct toxicity in animal cells.

From the above findings, it is considered that PSC-A is very useful as an agent for protecting against P. aeruginosa infection.

In the following, the method for manufacturing PSC-A will be described according to examples and the utility of PSC-A as an agent for protecting against P. aeruginosa infection will be described according to experimental examples.

EXAMPLE 1

Preparation of PSC-A from P. aeruginosa of Serotype E

The medium for the culture of P. aeruginosa was contained (per liter) 20 g of sodium glutamate, 5 g of glycerin, 0.1 g of $MgSO_4.7H_2O$, 0.55 g of $KH_2PO_4$, 5.6 g of $Na_2HPO_4.12H_2O$, 17.26 mg of $Ca(NO_3)_2.4H_2O$ and 50 μg of $FeSO_4.7H_2O$, and was adjusted to pH 7.6.

After P. aeruginosa ATCC27581 (E type) was cultured on a nutrient agar medium at 37° C. overnight, microbial cells were suspended in physiological saline.

The, 0.5 ml of the suspension was inoculated into a Sakaguchi's flask containing 150 ml of the synthetic medium having the above composition, and shaking culture was performed at 37° C. for 16 hours.

After the cultivation 1.2 ml of formalin was added to the culture of the flask, then the culture was thoroughly mixed before being left at room temperature for one hour. Then the culture was subjected to centrifugation (12,000×g, 30 minutes) to collect microbial cells. After that, by washing of the microbial cells with physiological saline and distilled water, 55 g of wet microbial cells was obtained from 15 L of culture medium. The wet microbial cells obtained thus were then suspended in 220 ml of 20 mM Tris-Hc buffer (pH 8.0) containing 2% of Triton X 100 and 10 mM of EDTA before being crushed with a DYNO-MILL (beads 0.1 mm φ) for three minutes while being cooled.

Next, the suspension of crushed microbial cells prepared thus was left at 4° C. and the supernatant was collected by decantation. The residue was suspended in 500 ml of above buffer and same procedure as above was repeated once. The supernatant collected thus was then pooled and centrifuged (39,000×g, 30 minutes).

Next, 720 ml of the supernatant was applied to an affinity column packed with affigel-10 (manufactured by Bio-Rad company) immobilized with monoclonal antibody C-Ab(column size, 22×40 mm; 15 mg of C-Ab was bound to 1 ml of Affigel-10).

The column was then washed with 100 ml of 20 mM Tris-HCl buffer (pH 8.0) containing 0.5% Triton X100 and 100 ml of 20 mM Tris-HCl buffer (pH 8.0), respectively and eluted with 60 mlof 50 mM glycine-HCl buffered saline (pH 3.0). The eluate obtained thus was then neutralized with 1N aqueous sodium hydrogen carbonate solution and dialyzed against distilled water at 4° C. for 24 hours. After that, the dialyzate was lyophilized to obtain 4.7 mg of a pure powder of PSC-A.

EXAMPLE 2

Preparation of PSC-A from P. aeruginosa of Serotype G

After P. aeruginosa ATCC 27584 (G type) was subjected to shaking culture in the synthetic medium (in the same way as in Example 1) at 37° C. for 20 hours. The below procedure was performed in the same way as in Example 1. 6.2 mg of PSC-A was obtained from 58.2 g of wet microbial cells.

The amino acid composition of PSC-A was determined by an automatic amino acid analyzer (IRICA A-5500) and the results are shown in Table 3.

TABLE 3

| Amino acid composition of PSC-A | |
|---|---|
| Amino acid | mole %* |
| Lysine | 10.07 |
| Histidine | 0.06 |
| Arginine | 1.45 |
| Aspartic acid or asparagine | 5.63 |
| Threonine | 5.07 |
| Serine | 3.59 |
| Glutamic acid or glutamine | 15.44 |
| Proine | 2.17 |
| Glycine | 7.42 |
| Alanine | 20.27 |
| Cystein | 0.00 |
| Valine | 1.57 |
| Methionine | 1.45 |
| Isoleucine | 4.18 |
| Leucine | 7.10 |
| Tyrosine | 0.46 |
| Phenylalanine | 1.94 |
| Tryptophan** | 2.12 |

*: based on duplicate analysis of 24-,48-, and 72-h hydrolysate (in 6N HCl at 105° C.)
**: determined by a spectrophotometric method (Anal. Chem., 29, 1193, 1957)

EXAMPLE 3

Preparation of SPC-A from P. aeruginosa of Serotype I

After P. aeruginosa ATCC 27586 (I type) was subjected to shaking culture in the synthetic medium (in the same way as in Example 1) at 37° C. for 20 hours. The below procedure was performed in the same way as in Example 1. 28 mg of PSC-A was obtained from 305 g of wet microbial cells.

EXAMPLE 4

Solution

After 1 mg of PSC-A obtained in Example 2 was dissolved in 10 ml of physiological saline, the solution prepared thus was subjected to aseptic filtration through a Nuclepore NO 20 (manufactured by Nuclepore company). A 1 ml sample of the filtrate obtained thus was then poured into each vial without allowing any contamination by bacteria to obtain a solution of PSC-A.

EXAMPLE 5

Lyophilized preparation

After 10 mg of PSC-A obtained in Example 3 was dissolved in 10 ml of distilled water, 500 mg of mannitol was added to the solution.

The solution was filtered through a Nuclepore NO 20. A 1 ml sample of the filtrate obtained thus was then poured into each vial without allowing any contamination by bacteria before lyophilization was performed to obtain a lyophilized preparation of PSC-A.

EXAMPLE 6

Emulsion

After 1 mg of PSC-A obtained in Example 3 was dissolved in 0.5 ml of physiological saline, 0.5 ml of mixture solution consisting of liquid paraffin and Arlacel (manufactured by Arlacel A. Atlas Chemical Industries) in a ratio of 8.5 to 1.5 was added to the solution and a water-in-oil type emulsion was prepared.

(Effect of This Invention)

EXPERIMENTAL EXAMPLE 2

Antigenic Property of PSC-A in Mice

Equal amounts of Freund incomplete adjuvant and a physiological saline solution of PSC-A obtained in Example 1 and that in Example 2 are mixed to prepare water-in-oil type emulsions, respectively.

After one group consisting of five BALB/1C female mice, 8 weeks old was immunized twice with each of the above emulsions at one-week intervals (10 μg per mouse of PSC-A was intraperitoneally administered for each immunization), blood was collected by eye bleeding (20 μl) from each mouse four days following the final immunization. The titer of anti-*P. aeruginosa* antibody in the serum of the mouse was determined by DIBA method described in Experimental Example 1. The results are shown in Table 4. After the immunization with PSC-A was performed, a high titer of the antibody was detected in the serum. The antibody was not detected in nonimmunized mice almost entirely.

TABLE 4

| Immunogen | Mouse No. | Antibody Titer in Mouse Serum determined by DIBA method* | | | |
|---|---|---|---|---|---|
| | | IID 1002 | ATCC 27581 | ATCC 10145 | ATCC 27586 |
| PSC-A in Example 1 | 1 | $5^3 \times 10^2$ | $5^4 \times 10^2$ | $5^4 \times 10^2$ | $5^4 \times 10^2$ |
| | 2 | $5^3 \times 10^2$ | $5^4 \times 10^2$ | $5^3 \times 10^2$ | $5^4 \times 10^2$ |
| | 3 | $5^3 \times 10^2$ | $5^3 \times 10^2$ | $5^3 \times 10^2$ | $5^3 \times 10^2$ |
| | 4 | $5^3 \times 10^2$ | $5^3 \times 10^2$ | $5^3 \times 10^2$ | $5^3 \times 10^2$ |
| | 5 | $5^3 \times 10^2$ | $5^4 \times 10^2$ | $5^4 \times 10^2$ | $5^3 \times 10^2$ |
| PSC-A in Example 2 | 6 | $5^3 \times 10^2$ | $5^3 \times 10^2$ | $5^4 \times 10^2$ | $5^3 \times 10^2$ |
| | 7 | $5^3 \times 10^2$ | $5^3 \times 10^2$ | $5^3 \times 10^2$ | $5^3 \times 10^2$ |
| | 8 | $5^3 \times 10^2$ | $5^4 \times 10^2$ | $5^4 \times 10^2$ | $5^3 \times 10^2$ |
| | 9 | $5^3 \times 10^2$ | $5^3 \times 10^2$ | $5^3 \times 10^2$ | $5^3 \times 10^2$ |
| | 10 | $5^3 \times 10^2$ | $5^3 \times 10^2$ | $5^3 \times 10^2$ | $5^3 \times 10^2$ |

*The antibody titer was determined by DIBA method using 0.3% -formalin- treated cells of *P. aeruginosa* IID1002 (B type), ATCC 27581 (E type), ATCC 10145 (G type) and ATCC 27586 (I type).
The antibody titer for each bacterial stain was expressed as the maximum multiple of dillution mouse serum for which dark blue spot was observed on a nitrocellulose membrane filter.

EXPERIMENTAL EXAMPLE 3

Effect of PSC-A on the protection against *P. aeruginosa* Infection (part 1)

After two groups each consisting of BALB/C female mice, 8 weeks old were immunized twice with each of the two emulsions shown in Experimental Example 2 at one-week intervals (10 μg per mouse of PSC-A was intraperitoneally administered for each immunization), each mouse was infected with *P. aeruginosa* (5 LD$_{50}$) one week following the final immunization. Two strains of *P. aeruginosa* PA103 (E type) and P 28 (C type) were used for the infection. Each of these strains was cultured on a heart infusion agar medium (manufactured by Eiken Kagaku) overnight and collected and diluted with physiological saline. The 5 pts. of mucin was added to 100 pts. of the bacterial suspension and each mouse was intraperitoneally inoculated with about a 5 LD$_{50}$ amount of the bacterial suspension prepared thus. For the control group, physiological saline alone was administered instead of PSC-A. The number of mice in each group remaining days following infection by *P. aeruginosa* was counted and the results are shown in Table 5. Thus PSC-A was effective for the protection against *P. aeruginosa* infection.

TABLE 5

| Test Groups | Immunogen | *P. aeruginosa* Used | Survival after 7 days | Survival Rate(*) |
|---|---|---|---|---|
| Control I | — | PA103 (E type) | 0/5 | 0 |
| Group I | PSC-A in Example 1 | PA103 (E type) | 5/5 | 100 |
| Group II | PSC-A in Example 2 | PA103 (E type) | 5/5 | 100 |
| Control II | — | P28(G type) | 0/5 | 0 |
| Group III | PSC-A in Example 1 | " | 5/5 | 100 |
| Group IV | PSC-A in Example 2 | " | 5/5 | 100 |

EXPERIMENTAL EXAMPLE 4

Effect of PSC-A on the protection against *P. aeruginosa* Infection (part 2)

PSC-A obtained in Example 3 was dissolved in physiological saline to prepare a sample solution. After two groups each consisting of five BALB/C female mice, 8 weeks old were immunized four times with the solution prepared thus at one-week intervals (20 μg per mouse of PSC-A was subcutaneously administered for each immunization), these two groups were infected with two strains of *P. aeruginosa* consisting of Pa103 (E type) and P28 (G type), respectively. A bacterial suspension of each of these strains was prepared in the same manner as in Example 3 and each mouse was infected with the bacterium by being intraperitoneally inoculated with an about 3 LD$_{50}$ amount of the bacterial suspension. For the control group, physiological saline alone was administered instead of PSC-A.

As seen in Table 6, PSC-A was effective for the protection against *P. aeruginosa* infection.

TABLE 6

| Test Groups | Immunogen | P. aeruginosa Used | Survival after 7 days | Survival Rate(*) |
|---|---|---|---|---|
| Control I | — | PA103 (E type) | 0/5 | 0 |
| Group I | PSC-A in Example 3 | PA103 (E type) | 4/5 | 80 |
| Control II | — | P28 (G type) | 0/5 | 0 |
| Group II | PSC-A in Example 3 | P28 (G type) | 5/5 | 100 |

EXPERIMENTAL EXAMPLE 5

Effect of PSC-A on the protection against *P. aeruginosa* infection (part 3)

Each of PSC-A obtained in Example 1 and that in Example 2 was dissolved in physiological saline to prepare sample solutions. Two groups each consisting of 15 female mice, 6 weeks old were immunized three times with each of the two sample solutions at one-week intervals (30 μg per mouse of PSC-A was intraperitoneally administered for each immunization). One week following the final immunization, each mouse was infected with *P. aeruginosa*. Two strains of *P. aeruginosa* PA103 (E type) and P28 (G type) were used for the infection similarly to Experimental Example 3 and 4. After suspension was prepared from these strains in the same manner as in Experimental Example 3, a 3 $LD_{50}$ and 5.5 $LD_{50}$ amount of the suspension from the PA103 and P28 strain was interaperitoneally inoculated into each mouse, respectively. For the control group, physiological saline alone was administered instead of PSC-A. The number of mice in each group remaining 7 days following infection by *P. aeruginosa* was counted and results are shown in Table 7. Thus PSC-A was effective for the protection against *P. aeruginosa* infection.

TABLE 7

| Test Groups | Immunogen | P. aeruginosa Used | Survival after 7 days | Survival Rate(*) |
|---|---|---|---|---|
| Control I | — | PA103 (E type) | 0/15 | 0 |
| Group I | PSC-A in Example 1 | PA103 (E type) | 15/15 | 100 |
| Group II | PSC-A in Example 2 | PA103 (E type) | 15/15 | 100 |
| Control II | — | P28 (G type) | 1/15 | 6.7 |
| Group III | PSC-A in Example 1 | P28 (G type) | 12/15 | 80 |
| Group IV | PSC-A in Example 2 | P28 (G tpe) | 11/15 | 73.3 |

EXPERIMENTAL EXAMPLE 6

Acute Toxicity

One group consisting of six BALB/C female mice, 5 weeks old was intravenously administered with a solution prepared by dissolving PSC-A in Example 3 in physiological saline. In the same way, LPS extracted from *E. coli* (lipopolysaccharide manufactured by Sigma company, serotype No. 0111 : B4) was intravenously administered to another mouse group. The $LD_{50}$ level of PSC-A and LPS for intravenous administration was observed during the 24 hours following the administration. The results are shown in Table 8. As distinct from LPS, PSC-A exhibited low toxicity.

TABLE 8

| Sample | $LD_{50}$ for Intravenous Administration |
|---|---|
| PSC-A | >5 mg/kg |
| LPS from *E. coli* | ≦0.1 mg/kg |

EXPERIMENTAL EXAMPLE 7

Pyrogenicity

One group consisting of three Japanese-while female rabbits was intravenously administered with a solution prepared by dissolving PSC-A in Example 3 in physiological saline. In the same way, LPS extracted from *E. coli* (lipopolysaccharide manufactured by Sigma company, serotype No. 0111 : B4) was intravenously administered to another rabbit group. The body temperature of each rabbit was successively measured from two hours before the administration until six hours after the administration. The results are shown in Table 9. The pyrogenicity of PSC-A was lower than that of LPS.

TABLE 9

| Sample | Minimum Dose for 0.6° C. increase of body temperature |
|---|---|
| PSC-A | $>1 \times 10^2$ μg/kg |
| LPS from *E. coli* | $1 \times 10^{-3}$ μg/kg |

What is claimed is:

1. PSC-A, a bacterial antigen obtained from *P. aeruginosa*, said antigen having the following properties:

a. amino acid composition:

| Amino acid composition of PSC-A | |
|---|---|
| Amino acid | mole % |
| Lysine | 10.07 |
| Histidine | 0.06 |
| Arginine | 1.45 |
| Aspartic acid or asparagine | 5.63 |
| Threonine | 5.07 |
| Serine | 3.59 |
| Glutamic acid or glutamine | 15.44 |
| Proline | 2.17 |
| Glycine | 7.42 |
| Alanine | 20.27 |
| Cystein | 0.00 |
| Valine | 11.57 |
| Methionine | 1.45 |
| Isoleucine | 4.18 |
| Leucine | 7.10 |
| Tyrosine | 0.46 |
| Phenylalanine | 1.94 |
| Tryptophan | 2.12 | b. a molecular weight as determined by SDS-polyacrylamide gel electrophoresis of about 15,000;

c. a lipid content of 7.0 to 10.0%;

d. a protein content of 55% as determined by colorimetric analysis by hydrolysis using ninhydrin;

e. a sugar content of 3.0 to 5.0%;

f. a hexosamine content of less than 1.0%;

g. an isoelectric point of pI=3.8–4.2 as determined by agarose electrofocusing;

h. stability in a neutral aqueous solution at room temperature for at least 24 hours;

i. maximum ultraviolet absorption at about 272 nm;

j. no decomposition of casein or collagen;

k. in appearance, a pale yellow powder soluble in water, physiological saline, and phosphate buffer, water soluble with a solubility of at least 1 mg/ml; and almost insoluble in methanol, ether, hexane, or chloroform;
l. producing a positive results in a Lowry-Folin reaction, ninhydrin reaction, phenol-sulfate reaction and anthron-sulfate reaction and a negative reaction in an Elson-Morgan reaction;
m. exhibiting no direct toxicity for either L cells of a cell line derived from mouse connective tissue before they are cultured for 24 hours or for leukocyte cells derived from the spleen of a normal mouse before they are cultured for 24 hours;
n. when said antigen is treated with pronase or heated at 100° C. for 10 minutes, there is not reaction with a serum from a mouse immunized with nontreated antigen;
o. an antibody which can react with P. aeruginosa appears in the serum of a mouse immunized with said antigen;
p. wherein the mouse monoclonal antibody having a specific affinity for PSC-A does not react with either the well-known common antigen OEP to P. aeruginosa or the endotoxin of P. aeruginosa (lipopolysaccharide).

2. A pharmaceutical composition containing PSC-A as an active ingredient and a pharmaceutically acceptable carrier for protecting against P. aeruginosa infection.

3. The composition as set forth in claim 2 where the PSC-A is obtained from microbial cells of P. aeruginosa.

* * * * *